United States Patent
Carballada et al.

(10) Patent No.: US 6,703,008 B2
(45) Date of Patent: *Mar. 9, 2004

(54) AEROSOL HAIR SPRAY COMPOSITIONS COMPRISING COMBINATIONS OF SILICONE-GRAFTED COPOLYMERS

(75) Inventors: Jose Antonio Carballada, Cincinnati, OH (US); Thomas Allen Hutchins, Cincinnati, OH (US)

(73) Assignee: The Procter & Gamble Company, Cincinnati, OH (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/263,014

(22) Filed: Mar. 5, 1999

(65) Prior Publication Data

US 2002/0015681 A1 Feb. 7, 2002

(51) Int. Cl.$^7$ ................................. A61K 7/11
(52) U.S. Cl. ................ 424/70.1; 424/70.11; 424/70.12; 424/70.121; 424/70.13; 424/70.18
(58) Field of Search .............. 424/70.11, 70.12, 424/70.121, 70.13, 70.16, 78.18, 45; 525/474

(56) References Cited

U.S. PATENT DOCUMENTS

| | | | |
|---|---|---|---|
| 4,192,862 A | 3/1980 | Pengilly | 424/47 |
| 4,988,506 A | 1/1991 | Mitra et al. | 424/81 |
| 5,021,477 A | 6/1991 | Garbe et al. | 424/70 |
| 5,061,481 A | 10/1991 | Suzuki et al. | 424/63 |
| 5,068,099 A | 11/1991 | Sramek | 424/47 |
| 5,166,276 A | 11/1992 | Hayama et al. | 525/329.7 |
| 5,219,560 A | 6/1993 | Suzuki et al. | 424/63 |
| 5,323,935 A | 6/1994 | Gosselin et al. | 222/401 |
| 5,480,634 A | 1/1996 | Hayama et al. | 424/70.12 |
| 5,565,193 A | 10/1996 | Midha et al. | 424/70.12 |
| 5,618,524 A | 4/1997 | Bolich, Jr. et al. | 424/70.12 |
| 5,653,968 A | 8/1997 | Carballada et al. | 424/70.11 |
| 5,653,969 A | 8/1997 | Carballada et al. | 424/70.16 |
| 5,658,557 A | 8/1997 | Bolich, Jr. et al. | 424/70.12 |
| 5,665,337 A | 9/1997 | Carballada et al. | 424/70.12 |
| 5,667,771 A | 9/1997 | Carballada et al. | 424/70.12 |
| 5,753,216 A | 5/1998 | Leitch et al. | 424/70.12 |
| 5,811,109 A * | 9/1998 | Cooper et al. | 424/401 |
| 6,011,126 A * | 1/2000 | Dubief et al. | 525/477 |
| 6,177,063 B1 * | 1/2001 | Hutchins | 424/47 |

FOREIGN PATENT DOCUMENTS

| | | | |
|---|---|---|---|
| EP | 412710 | 2/1991 | A61K/7/48 |
| EP | 0 878 184 A2 | 11/1998 | A61K/7/06 |

OTHER PUBLICATIONS

U.S. patent application Ser. No. 08/410,599, Bolich et al., filed Jun. 8, 1994.
U.S. patent application Ser. No. 08/496,998, Peffly, filed Jun. 30, 1995.
U.S. patent application Ser. No. 08/644,937, Peffly, filed May 13, 1996.
U.S. patent application Ser. No. 08/807,845, Midha et al., filed Feb. 26, 1997.
U.S. patent application Ser. No. 08/877,967, Bolich et al., filed Jun. 18, 1997.
U.S. patent application Ser. No. 08/877,975, Torgerson et al., filed Jun. 18, 1997.
U.S. patent application Ser. No. 09/067,637, Hutchins, filed Apr. 28, 1998.

* cited by examiner

Primary Examiner—Theodore J. Criares
Assistant Examiner—Gina C Yu
(74) Attorney, Agent, or Firm—Linda M. Sivik

(57) ABSTRACT

Disclosed are aerosol hair spray compositions which comprise a first and a second silicone-grafted copolymer, wherein the copolymers exhibit a dichotomous viscosity behavior which results in superior hold and excellent hair feel benefits, and a method of styling hair comprising applying to the hair an effective amount of the above composition. The aerosol hair spray compositions comprise: (A) from about 0.1% to about 10% by weight of said composition, of a first silicone-grafted copolymer comprising a vinyl polymeric backbone and a polysiloxane macromer grafted to said vinyl polymeric backbone, (i) wherein said first silicone-grafted copolymer is formed from the copolymerization of randomly repeating hydrophilic monomer units, herein designated A, and hydrophobic monomer units, herein designated B, (a) wherein said vinyl polymeric backbone comprises from about 10% to about 50%, by weight of said first silicone-grafted copolymer, of copolymerizable hydrophilic A monomers, (b) wherein said vinyl polymeric backbone comprises from 0% to about 85%, by weight of said first silicone-grafted copolymer, of copolymerizable hydrophobic B monomers, (c) wherein said polysiloxane macromer comprises from about 5% to about 50%, by weight of said first silicone-grafted copolymer, of polysiloxane-containing monomer units, (ii) wherein said polysiloxane macromer has a weight average molecular weight from about 500 to about 50,000; and (iii) wherein said first silicone-grafted copolymer has a weight average molecular weight from about 10,000 to about 500,000; (B) from about 0.1% to about 5% by weight of said composition, of a second silicone-grafted copolymer, comprising a vinyl polymeric backbone and a polysiloxane macromer grafted to said vinyl polymeric backbone, (i) wherein said second silicone-grafted copolymer is formed from the copolymerization of randomly repeating hydrophobic monomer units, herein designated B, (ii) wherein said polysiloxane macromer comprises from about 10% to about 40%, by weight of said second silicone-grafted copolymer, of polysiloxane-containing monomer units, (iii) wherein said polysiloxane macromer has a weight average molecular weight from about 5,000 to about 50,000, (iv) wherein said second silicone-grafted copolymer has a weight average molecular weight from about 300,000 to about 5,000,000, and (v) wherein said first silicone-grafted copolymer is present, relative to said second silicone-grafted copolymer, by weight, in a ratio from about 2:1 to about 26:1; (C) a neutralizing system, (D) from about 20% to about 50%, by weight of said composition, of a propellant; and (E) the balance comprising a carrier.

19 Claims, No Drawings

400
AEROSOL HAIR SPRAY COMPOSITIONS COMPRISING COMBINATIONS OF SILICONE-GRAFTED COPOLYMERS

TECHNICAL FIELD

The present invention relates to aerosol hair spray compositions which comprise a first and a second silicone-grafted copolymer, having defined molecular weights, and present in a specific ratio to each other, wherein the copolymers impart a dichotomous viscosity behavior to the hair spray. In particular, the hair spray exhibits certain viscosity characteristics when it is dispensed from the can and other viscosity characteristics when it is present on the hair. This dichotomous behavior results in superior hold and excellent hair feel benefits, upon application of the hair spray composition.

BACKGROUND OF THE INVENTION

Hair styling compositions are well known in the art and are commercially available in a variety of forms, including, for example, mousses, gels, lotions, and hair sprays. Many of these compositions contain hair styling resins to provide temporary hair styling or "setting" benefits.

Silicone-grafted copolymers are known in the art to be particularly effective hair styling resins because these copolymers can provide good style retention benefits to the hair while also providing desirable hair feel. In particular, silicone-grafted copolymers can impart a tactile sense of softness and conditioning relative to more conventional, non-silicone-containing resins. Silicone-grafted copolymers are typically used as neutralized copolymers because, when these copolymers are used in at least partially neutralized form, the copolymers provide for a hair spray composition that is easily removable by water and/or by shampooing and that has good styling performance. U.S. Pat. No. 5,565,193 (Midha), issued on Oct. 15, 1996, teaches hair spray compositions which incorporate silicone grafted copolymers.

While hair spray compositions which contain silicone-grafted copolymers provide a superior combination of good styling and desirable hair feel relative to hair sprays which incorporate other types of resins, consumers nevertheless desire hair spray products which provide even better styling and hair feel benefits. Unfortunately, a better combination of styling and hair feel than is achieved by the incorporation of silicone-grafted copolymers is difficult to achieve.

The viscosity of the hair spray is an important element with respect to both styling and hair feel. In general, the lower the viscosity of the hair spray composition as it is present on the hair, the better (i.e., less sticky) the hair feel. This is because the low viscosity of the composition allows it to wick and spread efficiently on the hair. However, low viscosity hair sprays typically result in small droplet size of the composition as it is dispensed from the can. Small droplet size generally results in a hair spray with decreased hold, while larger droplet size is typically associated with increased hold. In these low viscosity systems, attempts to increase the droplet size by utilizing alternative inserts and spray buttons have not delivered the desired droplet size and may lead to other non-desirable changes in other properties of the hair spray as well, negatively impacting hair feel and hold. Therefore, from the standpoint of styling, hair spray compositions which have high viscosity at the point at which they are dispensed from the can are preferred.

One way to deliver a hair spray with increased styling and hair feel above and beyond what is achieved by the incorporation of silicone-grafted copolymers would be to impart dichotomous viscosity characteristics to the hair spray. In other words, develop a hair spray composition having a high viscosity when it is dispensed from the aerosol can (i.e., under high shear conditions), but having a low viscosity upon being deposited to the hair (i.e., under low shear conditions).

Past attempts to achieve the benefits of a dual viscosity system in a hair spray have failed. Attempts to increase the high shear viscosity of a low viscosity hair spray composition in order to increase hold, such as by making the composition more concentrated or by increasing the molecular weight of the silicone-grafted copolymer, have resulted in higher viscosity at low shear as well, thereby negatively impacting the hair feel imparted by the hair spray composition.

Applicants have now found a way, however, to impart the aforementioned dual viscosity characteristics to a hair spray composition and to provide hair spray compositions which provide a superior combination of styling and hair feel above and beyond that which is achieved by the mere incorporation of a silicone-grafted copolymer into a hair spray. These characteristics are achieved by blending a first silicone-grafted copolymer with a second silicone-grafted copolymer, wherein the monomers which form the respective silicone-grafted copolymers are present in the copolymers in a particular weight percentage and wherein the first and second silicone-grafted copolymers are present in the hair spray composition at a particular ratio with respect to one another.

Hair spray compositions which contain blends of silicone-grafted copolymers are generally described in U.S. Pat. No. 5,618,524 (Bolich), issued on Apr. 8, 1997. However, the '524 patent does not specifically teach silicone-grafted polymers wherein the monomers are present at ratios as described herein and, accordingly, the hair spray compositions taught therein do not necessarily deliver the same combination of good styling and good hair feel as the compositions of the present invention.

It is an object of this invention to provide hair spray formulations that exhibit a dichotomous viscosity behavior at high shear and at low shear, which results in superior hold and excellent hair feel benefits. It is also an object of this invention to provide a method for styling hair. These, and other objects will become readily apparent from the detailed description below.

SUMMARY OF THE INVENTION

The present invention relates to aerosol hair spray compositions which provide excellent styling and hair feel benefits. These hair spray compositions comprise: (A) from about 0.1% to about 10%, by weight, of a first silicone-grafted copolymer; (B) from about 0.1% to about 5%, by weight, of a second silicone-grafted copolymer; (C) a neutralizing system comprising at least one base selected from the group consisting of an organic base, an inorganic base, and mixtures thereof, wherein the system is present at a level sufficient to neutralize from about 30% to about 95% of the acid groups on the first silicone-grafted copolymer; (D) from about 20% to about 50%, by weight, of a propellant; and (E) the balance comprising a carrier, wherein the carrier is suitable for solubilizing the first and second silicone-grafted copolymers, and the carrier is suitable for application to hair.

The first silicone-grafted copolymer has a weight average molecular weight from about 10,000 to about 500,000. It comprises a vinyl polymeric backbone and a polysiloxane macromer grafted to the backbone. The vinyl polymeric backbone is formed from the copolymerization of randomly repeating hydrophilic monomer units, hereinbelow designated A, and may additionally include randomly repeating hydrophobic monomer units, hereinbelow designated B. The vinyl polymeric backbone comprises from about 10% to about 50%, by weight of the copolymer, of copolymerizable (hydrophilic) A monomers, and from 0% to about 85%, by weight of the copolymer, of copolymerizable (hydrophobic) B monomers. The polysiloxane macromer comprises from about 5% to about 50%, by weight of the copolymer, of polysiloxane-containing monomer units, and has a weight average molecular weight from about 500 to about 50,000.

The second silicone-grafted copolymer has a weight average molecular weight from about 300,000 to about 5,000,000. It also comprises a vinyl polymeric backbone and a polysiloxane macromer grafted to the backbone. The vinyl polymeric backbone is formed from the copolymerization of randomly repeating (hydrophobic) B monomer units. The polysiloxane macromer comprises from about 10% to about 40%, by weight of the copolymer, of polysiloxane-containing monomer units, and has a weight average molecular weight from about 5,000 to about 50,000. The vinyl polymeric backbone of the second silicone-grafted copolymer contains essentially no (hydrophilic) A monomers. The first silicone-grafted copolymer is present, relative to the second silicone-grafted copolymer, by weight, in a ratio from about 2:1 to about 26:1.

The present invention further relates to a method of styling hair comprising applying to the hair an amount of the above-described composition which is effective to provide styling benefits.

DETAILED DESCRIPTION OF THE INVENTION

The aerosol hair spray compositions of the present invention provide a combination of excellent styling and hair feel benefits. This combination of benefits is achieved because the compositions herein are formulated so that they exhibit dichotomous viscosity characteristics. By "dichotomous viscosity characteristics" is meant that the hair spray compositions exhibit high viscosity characteristics under high shear conditions (e.g., at the point at which they are dispensed from the aerosol can), but exhibit low viscosity characteristics under low shear conditions (e.g., as present on hair).

The aerosol hair spray compositions of the present invention can comprise, consist of, or consist essentially of the essential elements and limitations of the invention described herein, as well as any of the additional or optional ingredients, components or limitations described herein.

In particular, the aerosol hair spray compositions of the present invention comprise A) a first silicone-grafted copolymer, B) a second silicone-grafted copolymer, C) a neutralizing system, D) a propellant, and E) a carrier. Each of these components, as well as methods for making and using the hair spray compositions herein, is described in detail below.

I. COMPONENTS
A. First Silicone-Grafted Styling Copolymer

The aerosol hair spray compositions of the present invention comprise from about 0.1% to about 10%, by weight of the composition, of a first silicone-grafted styling copolymer. These copolymers are characterized by polysiloxane moieties covalently bonded to and pendant from a polymeric carbon-based backbone.

The first silicone-grafted copolymers suitable for use herein comprise "silicone-containing" (or "polysiloxane-containing") monomers, which form the silicone macromer pendant from the backbone, and non-silicone-containing monomers, which form the organic backbone of the polymer. The non-silicone-containing monomer units for the first silicone-grafted copolymer can be derived from (hydrophilic) A monomer units. They may also include (hydrophobic) B monomer units. Therefore, the silicone-grafted copolymers for use herein can comprise combinations of the (hydrophilic) A and polysiloxane-containing monomer units described herein, with or without (hydrophobic) B monomers as described herein, provided that the resulting styling polymer has the requisite characteristics as described herein.

As used herein, "(hydrophilic) A monomers" are those monomers selected from the group consisting of unsaturated organic mono- and polycarboxylic acids, unsaturated (meth) acrylate alcohols, unsaturated organic acid anhydrides, and mixtures thereof. As used herein, "(hydrophobic) B monomers" are those monomers selected from the group consisting of acrylic acid esters, methacrylic acid esters, vinyl compounds, vinylidene compounds, unsaturated hydrocarbons, $C_1$–$C_{18}$ alcohol esters or organic acids, organic acid anhydrides, and mixtures thereof.

The first silicone-grafted copolymers generally comprise from about 5% to about 50%, preferably from about 5% to about 40%, more preferably from about 10% to about 25%, by weight of the copolymer, of polysiloxane-containing monomer units; from about 10% to about 50%, preferably from about 10% to about 30%, more preferably from about 15% to about 25%, by weight of the copolymer, of (hydrophilic) A monomers. The first copolymers generally comprise from 0% to about 85%, preferably from about 30% to about 85%, more preferably from about 50% to about 75%, by weight of the copolymer, of (hydrophobic) B monomers. The total level of (hydrophilic) A monomers and (hydrophobic) B monomers is preferably from about 50% to about 95%, more preferably from about 60% to about 95%, most preferably from about 75% to about 90%, by weight of the copolymer.

The first silicone-grafted copolymers preferred for use herein are such that when formulated into the finished hair spray composition, and dried, the copolymers phase separate into a discontinuous phase which includes the polysiloxane macromer and a continuous phase which includes the backbone. It is believed that this phase separation property provides a specific orientation of the copolymer on the hair which results in the desired conditioning and styling benefits.

Silicone-grafted copolymers of the type incorporated into the hair spray compositions herein and referred to herein as "first silicone-grafted copolymers" are known in the art. See U.S. Pat. Nos. 5,618,524 (Bolich), issued on Apr. 8, 1997, and 5,658,557 (Bolich), issued on Aug. 19, 1997, both of which are incorporated herein by reference, in their entirety. The silicone-grafted styling copolymers provide a thin polymeric film on the hair from the hair spray composition which is removable with a shampoo.

The polymeric backbone and silicone marcromer components of these first silicone-grafted copolymers, as well as characteristics of the copolymers are described in further detail below.

i. Polymeric Backbone

The polymeric backbone of the first silicone-grafted copolymer is an organic backbone, preferably a carbon chain backbone derived from polymerization of ethylenically unsaturated monomers, such as a vinyl polymeric backbone, but can also include cellulosic chains or other carbohydrate-derived polymeric chains to which polysiloxane moieties are pendant. The backbone can also include ether groups, ester groups, urethane groups, and the like.

The first silicone-grafted copolymer is formed from (hydrophilic) A monomers, as described above. Importantly, the first silicone-grafted copolymer must contain at least about 10%, by weight of the copolymer, of copolymerizable (hydrophilic) A monomers.

Specific non-limiting examples of suitable (hydrophilic) A monomers include, but are not limited to, acrylic acid, methacrylic acid, maleic acid, maleic anhydride, half esters of maleic anhydride, crotonic acid, and itaconic acid. These monomers are carbon based and contain acid functional groups which are neutralizable with the neutralizing system defined below. Preferred (hydrophilic) A monomers include acrylic acid, methacrylic acid, and mixtures thereof.

Non-limiting examples of suitable (hydrophobic) B monomers include, but are not limited to, acrylic or methacrylic acid esters of $C_1$–$C_{18}$ alcohols such as methanol, ethanol, methoxy ethanol, 1-propanol, 2-propanol, 1-butanol, 2-methyl-1-propanol, 1-pentanol, 2-pentanol, 3-pentanol, 2-methyl-1-butanol, 1-methyl-1-butanol, 3-methyl-1-butanol, 1-methyl-1-pentanol, 2-methyl-1-pentanol, 3-methyl-1-pentanol, t-butanol (2-methyl-1-propanol), cyclohexanol, neodecanol, 2-ethyl-1-butanol, 3-heptanol, benzyl alcohol, 2-octanol, 6-methyl-1-heptanol, 2-ethyl-1-hexanol, 3,5-dimethyl-1-hexanol, 3,5,5-trimethyl-1-hexanol, 1-decanol, 1-dodecanol, 1-hexadecanol, 1-octadecanol, and the like, the alcohols having from about 1–18 carbon atoms with the average number of carbon atoms being from about 4–12; styrene; polystyrene macromer; vinyl acetate; vinyl chloride; vinylidene chloride; vinyl propionate; α-methylstyrene; t-butylstyrene; butadiene; cyclohexadiene; ethylene; propylene; vinyl toluene; and mixtures thereof. Preferred (hydrophobic) B monomers include n-butyl methacrylate, isobutyl methacrylate, 2-ethylhexyl methacrylate, methyl methacrylate, t-butylacrylate, t-butylmethacrylate, and mixtures thereof.

The vinyl polymeric backbone of the first silicone-grafted copolymer preferably has a glass transition temperature ($T_g$) or crystalline melting point ($T_m$) of at least about $-20°$ C., preferably from about 20° C. to about 80° C., more preferably from about 20° C. to about 60° C. Styling polymers having these $T_g$ or $T_m$ values form styling films on hair that are not unduly sticky or tacky to the touch. As used herein, the abbreviation "$T_g$" refers to the glass transition temperature of the backbone of the polymer, and the abbreviation "$T_m$" refers to the crystalline melting point of the backbone, if such a transition exists for a given polymer. Preferably, both the $T_g$ and the $T_m$, if any, are within the ranges recited above.

ii. Silicone-Containing Macromer

The first silicone-grafted copolymer also comprises a polysiloxane macromer (especially preferred are polydialkylsiloxane, most preferably polydimethylsiloxane) grafted to the backbone. The polysiloxane moieties can be substituted on the polymer or can be made by copolymerization of polysiloxane-containing polymerizable monomers with non-polysiloxane-containing polymerizable monomers.

Suitable polymerizable polysiloxane-containing monomers for the first silicone-grafted copolymers include, but are not limited to, those monomers that conform to the formula:

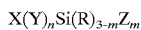   (I)

wherein X is an ethylenically unsaturated group, such as a vinyl group, which is copolymerizable with the non-silicone-containing monomers described herein; Y is a divalent linking group; R is a hydrogen, lower alkyl (e.g. $C_1$–$C_4$), aryl, alkylamino, tri ($C_1$–$C_4$ alkyl)siloxy or $C_1$–$C_4$ alkoxy; Z is a monovalent siloxane polymeric moiety; n is 0 or 1; and m is an integer from 1 to 3. These polymerizable polysiloxane-containing monomers have a weight average molecular weight as described above.

Preferably the polysiloxane-containing monomer is selected from one or more monomers that conform to the following formulas (II to VII):

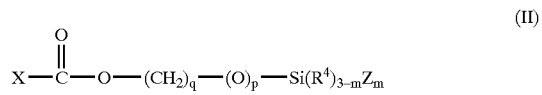 (II)

 (III)

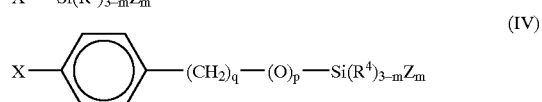 (IV)

 (V)

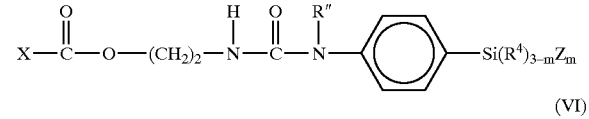 (VI)

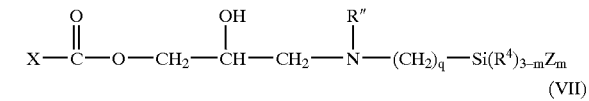 (VII)

wherein m is 1, 2 or 3 (preferably m=1); p is 0 or 1; q is an integer from 2 to 6; R" is alkyl or hydrogen, X conforms to the formula:

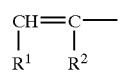

wherein $R^1$ is hydrogen or —COOH (preferably $R^1$ is hydrogen); $R^2$ is hydrogen, methyl or —CH$_2$COOH (preferably $R^2$ is methyl); Z conforms to the formula:

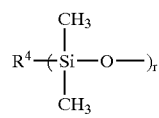

wherein $R^4$ is alkyl, alkoxy, alkylamino, aryl, or, hydroxyl (preferably $R^4$ is alkyl); and r is an integer of about 5 to about 700, preferably about 50 to about 500 (more preferably r is from about 150 to about 300). Of the above formulas, formula II is most preferred, particularly when p=0, and q=3.

The polysiloxane macromer for the first silicone-grafted copolymer should have a weight average molecular weight of at least about 500, preferably from about 1,000 to about 50,000, more preferably from about 5,000 to about 40,000, most preferably about 10,000 to about 20,000.

Preferred first silicone-grafted copolymers comprise monomer units derived from at least one free radically polymerizable vinyl (hydrophobic) B monomer and at least one (hydrophilic) A monomer which is copolymerizable with the vinyl monomer, and at least one polysiloxane macromer. Other examples of suitable silicone-grafted copolymers and their methods of preparation are described in U.S. Pat. No. 4,693,935 (Mazurek), issued Sep. 15, 1987; and U.S. Pat. No. 4,728,571 (Clemens), issued Mar. 1, 1988, which descriptions are incorporated herein by reference.

iii. Characteristics, Preparation, and Examples of First Silicone-Grafted Copolymer The first silicone-grafted copolymers preferably have a weight average molecular weight from about 10,000 to about 500,000, more preferably from about 50,000 to about 300,000, even more preferably from about 90,000 to about 165,000. The concentration of the first silicone-grafted copolymer in the hair spray composition should be sufficient to provide the desired hair styling performance, and generally ranges for the first copolymer, from about 0.1% to about 10%, preferably from about 2% to about 9%, more preferably from about 3% to about 7%, by weight of the composition.

The first silicone-grafted copolymers can be made by any conventional or otherwise known polymerization techniques well known in the art. The first silicone-grafted copolymers described above, and the second silicone-grafted copolymers described below, can be synthesized by free radical polymerization of silicone- or polysiloxane-containing monomers with non-silicone- or non-polysiloxane-containing monomers. The general principles of free radical polymerization methods are well understood. See Odian, "Principles of Polymerization", 3d. ed., John Wiley & Sons, (1991), at 198–334.

Non-limiting examples of some preferred first silicone-grafted copolymers for use in the aerosol hair spray compositions herein are listed below. Each listed polymer is followed by its monomer composition as part by weight of monomer used in the synthesis:

(i) t-butyl acrylate/acrylic acid/polydimethylsiloxane macromer—10,000 wt. avg. mw macromer (60/20/20);
(ii) t-butyl acrylate/acrylic acid/polydimethylsiloxane macromer—10,000 wt. avg. mw macromer (70/10/20);
(iii) t-butyl methacrylate/acrylic acid/polydimethylsiloxane macromer—10,000 wt. avg. mw macromer (65/15/20);
(iv) t-butyl acrylate/acrylic acid/polydimethylsiloxane macromer—10,000 wt. avg. mw macromer (75/15/10);

It may be desirable to purify the first silicone-grafted copolymer by removing unreacted silicone-containing monomer and silicone macromer-grafted polymer with viscosities at 25° C. of about 10,000,000 centistokes and less. This can be done, for example, by hexane extraction. After drying the resin from its reaction solvent, hexane extraction of the reaction product can be performed by adding an excess of hexane to the reaction product and heating to near the $T_g$ of the non-silicone portion of the polymer. The mixture is held at this temperature with stirring for about 30 minutes and cooled to room temperature. The hexane is removed by vacuum suction. Two more hexane extraction cycles are preferably conducted in the same manner as above. After the third cycle, residual hexane remaining with the product is removed by distillation and vacuum drying.

Low molecular weight polysiloxane-containing monomer and polymer is solubilized by supercritical carbon dioxide and transported away from the remaining polymer via a transfer line, which is maintained at identical temperature and pressure as the extraction vessel. The extracted materials are collected in an extraction vessel. Following extraction, the system is depressurized and dry, extracted copolymer is recovered from the extraction vessel.

B. Second Silicone-Grafted Styling Copolymer

The aerosol hair spray compositions of the present invention comprise from about 0.1% to about 5%, by weight of the composition, of a second silicone-grafted styling copolymer. When blended with the first silicone-grafted copolymer, at ratios specified herein, the second silicone-grafted copolymers provide a thin polymeric film on the hair from the hair spray composition which is removable with a shampoo.

These copolymers, like the first silicone-grafted copolymers, are known in the art, and are also characterized by polysiloxane moieties covalently bonded to and pendant from a polymeric carbon-based backbone.

Like the first silicone-grafted copolymers, the second silicone-grafted copolymers comprise "silicone-containing" (or "polysiloxane-containing") monomers, which form the silicone macromer pendant from the backbone, and non-silicone-containing monomers, which form the organic backbone of the polymer. The non-silicone-containing monomer units for the second silicone-grafted copolymer can be derived from (hydrophobic) B monomer units. Therefore, the second silicone-grafted copolymers for use herein can comprise combinations of the (hydrophobic) B and polysiloxane-containing monomer units described herein, provided that the resulting styling polymer has the requisite characteristics as described herein. However, unlike the first silicone-grafted copolymers, the second silicone-grafted copolymers are essentially free of (hydrophilic) A monomers.

The second silicone-grafted styling copolymers generally comprise from about 10% to about 40%, preferably from about 10% to about 30%, more preferably from about 15% to about 25%, by weight of the copolymer, of polysiloxane-containing monomer units.

The second silicone-grafted copolymers preferred for use herein are such that when formulated into the finished hair spray composition, and dried, the copolymers phase separate into a discontinuous phase which includes the polysiloxane macromer and a continuous phase which includes the backbone.

The polymeric backbone and silicone macromer components of these second silicone-grafted copolymers, as well as characteristics of the copolymers are described in further detail below.

i. Polymeric Backbone

The polymeric backbone of the second silicone-grafted copolymer is an organic backbone, preferably a carbon chain derived from polymerization of ethylenically unsaturated monomers, such as vinyl polymeric backbone, but can also include cellulosic chains or other carbohydrate-derived polymeric chains to which polysiloxane moieties are pendant. The backbone can also include ether groups, ester groups, urethane groups, and the like. The backbone of the second silicone-grafted copolymer is essentially free of (hydrophilic) A monomers.

The vinyl polymeric backbone of the second silicone-grafted copolymer preferably has a glass transition temperature ($T_g$) or crystalline melting point ($T_m$) of at least about −20° C., preferably from about 20° C. to about 80° C., more preferably from about 20° C. to about 60° C. Preferably, both the $T_g$ and the $T_m$, if any, are within the ranges recited above.

ii. Silicone-Containing Macromer

The second silicone-grafted copolymer also comprises a polysiloxane macromer (especially preferred are polydialkylsiloxane, most preferably polydimethylsiloxane)

grafted to the backbone. The polysiloxane moieties can be substituted on the polymer or can be made by co-polymerization of polysiloxane-containing polymerizable monomers with non-polysiloxane-containing polymerizable monomers.

Suitable polymerizable polysiloxane-containing monomers for the second silicone-grafted copolymers include, but are not limited to, those monomers that conform to the formula:

$$X(Y)_n Si(R)_{3-m} Z_m \quad (I)$$

wherein X is an ethylenically unsaturated group, such as a vinyl group, which is copolymerizable with the non-silicone-containing monomers described herein; Y is a divalent linking group; R is a hydrogen, lower alkyl (e.g. $C_1$–$C_4$), aryl, alkylamino, tri ($C_1$–$C_4$ alkyl)siloxy or $C_1$–$C_4$ alkoxy; Z is a monovalent siloxane polymeric moiety; n is 0 or 1; and m is an integer from 1 to 3. These polymerizable polysiloxane-containing monomers have a weight average molecular weight as described above.

Preferably the polysiloxane-containing monomer is selected from one or more monomers that conform to the following formulas (II to VII):

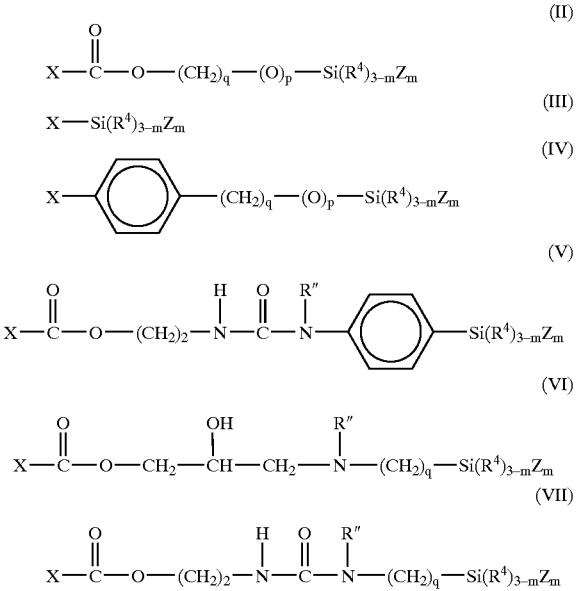

wherein m is 1, 2 or 3 (preferably m=1); p is 0 or 1; q is an integer from 2 to 6; R″ is alkyl or hydrogen, X conforms to the formula:

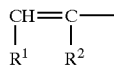

wherein $R^1$ is hydrogen or —COOH (preferably $R^1$ is hydrogen); $R^2$ is hydrogen, methyl or —CH$_2$COOH (preferably $R^2$ is methyl); Z conforms to the formula:

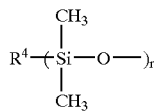

wherein $R^4$ is alkyl, alkoxy, alkylamino, aryl, or, hydroxyl (preferably $R^4$ is alkyl); and r is an integer of about 60 to about 700, preferably about 60 to about 400 (more preferably r is from about 100 to about 350). Of the above formulas, formula II is most preferred, particularly when p=0, and q=3.

The polysiloxane macromer for the second copolymer should have a weight average molecular weight from about 5,000 to about 50,000, preferably from about 5,000 to about 30,000, most preferably about 8,000 to about 25,000.

iii. Characteristics, Preparation, and Examples of First Silicone-Grafted Copolymer The second silicone-grafted polymers preferably have a weight average molecular weight from about 300,000 to about 5,000,000, more preferably from about 500,000 to about 2,000,000, even more preferably from about 600,000 to about 1,500,000. The concentration of the second silicone-grafted copolymer in the hair spray composition should be sufficient to provide the desired hair styling performance, and generally ranges for the second copolymer, from about 0.1% to about 5%, preferably from about 0.25% to about 3%, more preferably from about 0.25% to about 1.5%, by weight of the composition.

The second silicone-grafted styling copolymers can be made by any conventional or otherwise known polymerization techniques well known in the art, including those techniques described above for the synthesis of the first silicone-grafted copolymers.

Non-limiting examples of some preferred second silicone grafted copolymers for use in the aerosol hair spray compositions herein are listed below. Each listed polymer is followed by its monomer composition as part by weight of monomer used in the synthesis:

(i) t-butyl acrylate/polydimethylsiloxane macromer—10,000 wt. avg. mw macromer (80/20);

(ii) t-butyl acrylate/polydimethylsiloxane macromer—10,000 wt. avg. mw macromer (75/25);

(iii) t-butyl acrylate/polydimethylsiloxane macromer—20,000 wt. avg. mw macromer (80/20);

(iv) t-butyl acrylate/polydimethylsiloxane macromer—10,000 wt. avg. mw macromer (85/15);

C. Neutralizing System

The aerosol hair spray compositions of the present invention comprise a neutralizing system comprising an organic base, an inorganic base, or mixtures thereof, to neutralize or partially neutralize the first silicone-grafted styling copolymer described herein.

The aerosol hair spray compositions of the present invention contain a total amount of a neutralizing system whereby from about 30% to about 95%, preferably from about 80% to about 95% of the acidic monomers of the first silicone-grafted copolymer are neutralized. Any conventional organic and inorganic base materials can be used in the hair spray compositions herein, provided that they are used in accordance with the requisite neutralization capacities described herein.

Non-limiting examples of suitable inorganic base materials for use herein include ammonium hydroxide, and hydroxides of alkali and alkaline earth metals including potassium hydroxide, sodium hydroxide, and mixtures thereof. Preferred inorganic base materials include potassium hydroxide, sodium hydroxide, and mixtures thereof.

Non-limiting examples of suitable organic base materials for use herein include amines, especially amino alcohols such as 2-amino-2-methyl-1,3-propanediol (AMPD), 2-amine-2-ethyl-1,3-propanediol (AEPD), 2-amino-2-methyl-1-propanol (AMP), 2-amino-1-butanol (AB), monethanolamine (MEA), diethanolamine (DEA), triethanolamine (TEA), monoisopropanolamine (MIPA), diisopropanolamine (DIPA), triisopropanolamine (TIPA), dimethyl steramine (DMS), dimethyl myristamine (DMM), dimethyl lauramine (DML), amino methyl propanol (AMP), and mixtures thereof. A preferred organic base material is amino methyl propanol.

The amount, in grams, of organic and inorganic base materials (Z) required to neutralize an acidic polymer can be deduced from calculations which take into account the acid value of the polymer (A); amount of polymer (W); mol wt of the base (B); mol wt of the acidic moiety (M) and the degree of neutralization required (N).

$$Z(g)=W \times A/100 \times 1/M \times B \times N \%$$

In the following example the amount of KOH required to neutralize 2.6 g of acrylic acid co-polymer (with an acid value of 20) to a level of 60% neutralization is calculated.

$$Z(g)=2.6 \times 20/100 \times 1/72 \times 56 \times 0.60$$

$$Z=0.24 \text{ g}$$

Note, the acid value can be experimentally determined by titrating a specific amount of the polymer with base or theoretically by considering the original acidic content of the copolymer e.g. a polymer with 20% of acid monomer has an acid value of 20.

D. Propellant

The aerosol hair spray compositions of the present invention comprise from about 20% to about 50%, by weight of the composition, of a propellant suitable for aerosol delivery of the hair spray composition to the desired application surface. It has been found that the spray performance benefits of aerosol hair spray compositions are improved by minimizing the concentration of the hydrocarbon propellants to less than about 10%, by weight of the composition. As used herein, "hydrocarbon propellants" are those liquifiable gases that contain only carbon and hydrocarbon atoms, most notably of which are propane, butane, and isobutane. The aerosol hair spray compositions of the present invention preferably contain less than about 10%, more preferably less than about 5%, and most preferably 0%, by weight of the composition, of hydrocarbon propellants. Non-limiting examples of suitable hydrocarbon propellants for use herein include n-butane, isobutane, supplied as A-31, by Exxon Corporation, and isobutane/propane, supplied as A-46, by Exxon Corporation, and mixtures thereof.

The total concentration of the non-hydrocarbon propellant in the aerosol hair spray composition can include one or more non-hydrocarbon propellants; the total non-hydrocarbon propellant concentration typically ranging from about 20% to about 50%, more preferably from about 35% to about 40%, by weight of the composition. As used herein, "non-hydrocarbon propellants" are all liquifiable gases suitable for use in topical application to human hair or skin, excluding the above-identified hydrocarbon propellants. Non-limiting examples of suitable non-hydrocarbon propellants for use herein include nitrogen, carbon dioxide, nitrous oxide, atmospheric gas, 1,2-difluoroethane (Hydrofluorocarbon 152A) supplied as Dymel 152A by E. I. Du Pont de'Nemours Corporation, dimethyl ether, and mixtures thereof. A preferred non-hydrocarbon propellant is dimethyl ether.

E. Carrier

The aerosol hair spray compositions of the present invention comprise a suitable liquid carrier, preferably a liquid carrier at concentrations ranging from about 35% to about 79.8%, preferably from about 50% to about 75%, more preferably from about 55% to about 70%, by weight of the composition. The liquid carrier for use herein can comprise any known or otherwise effective liquid carrier for use in aerosol formulations intended for topical application to human hair or skin, e.g. liquid carriers for use in aerosol hair spray formulations. The liquid carrier can include solvents and other optional ingredients of the hair spray compositions of the present invention. However, it is preferred that the aerosol hair spray compositions contain less than about 3% water.

Suitable liquid carriers for use in the aerosol hair spray compositions of the present invention include organic solvents, such as $C_1$–$C_6$ alkanols, carbitol, acetone, $C_7$–$C_{10}$ isoparraffins, and mixtures thereof. Preferred liquid carriers are the $C_1$–$C_6$ alkanols and $C_7$–$C_{10}$ isoparraffins. Non-limiting examples of preferred $C_1$–$C_6$ alkanols include $C_2$–$C_4$ monohydric alcohols, such as ethanol, isopropanol, and mixtures thereof. Non-limiting examples of preferred $C_7$–$C_{10}$ isoparraffins are Isopar C™, Isopar E™, and Isopar G™, all available from Exxon Corporation.

II. Optional Components

A. Plasticizer

The aerosol hair spray compositions of the present invention may, in some embodiments, comprise a non-volatile plasticizer at concentrations effective to provide for improved hair style performance. Such concentrations generally range from 0% to about 2%, preferably from about 0.2% to about 0.6%, by weight of the composition. As used herein, "non-volatile" in regard to plasticizers means that the plasticizer does not have a measurable vapor pressure under ambient conditions. The copolymer-liquid carrier solution should not suffer from substantial plasticizer weight loss while the liquid carrier is evaporating, since this may excessively reduce plasticization of the copolymer during use.

The plasticizers for use herein should generally have boiling points greater than or equal to about 250° C. These materials are well known in the art and are described in *Kirk-Othmer Encyclopedia of Chemical Technology*, 2d ed., vol. 15, at 720–789 (John Wiley & Sons, Inc. New York, (1968)) under the topic heading "Plasticizers"; in *The Technology of Plasticizers*, by J. Kern Sears and J. R. Darby (John Wiley & Sons, Inc., New York, (1982)); and in the Appendix of Sears/Darby, Table A.9, at 983–1063; which descriptions are incorporated herein by reference.

The plasticizers suitable for use in the aerosol hair spray compositions of the present invention include both cyclic and acyclic non-volatile materials. Non-limiting examples of suitable non-volatile plasticizers include adipates, phthalates, isophthalates, azelates, stearates, citrates, trimellitates, silicone copolyols, iso- $C_{14}$–$C_{22}$ alcohols, carbonates, sebacates, isobutyrates, oleates, phosphates, myristates, ricinoleates, pelargonates, valerates, camphor, glycols, glycerin, citrates, and castor oil.

Preferred plasticizers for use herein include diisobutyladipate (DIBA), and glycols. Preferred glycols include propylene glycol, dipropylene glycol and mixtures thereof.

B. Conditioning Agent

The aerosol hair spray compositions of the present invention may, in some embodiments, further comprise a conditioning agent at concentrations effective to modify hair feel. Such concentrations generally range from about 0.01% to about 5%, by weight of the composition. Useful conditioning agents include silicone and silicone copolyols. Additionally, vitamin $B_5$ alcohols may be used, preferably panthenol.

The silicone conditioning agent may comprise a silicone fluid and may also comprise other ingredients, such as a silicone resin to enhance silicone fluid deposition efficiency or to enhance glossiness of the hair. These additional efficiency and gloss benefits are provided especially, when high refractive index (i.e. above about 1.46) silicone conditioning agents are used. A preferred high refractive index silicone conditioning agent is phenyl trimethicone.

The silicone conditioning agent may comprise a volatile silcone, a non-volatile silicone, and mixtures thereof. Silicone fluids suitable for use herein include silicone oils which are flowable silicone materials with a viscosity of less than about 1,000,000 centistokes, preferably between about 5 and about 1,000,000 centistokes, more preferably between about 10 and about 600,000 centistokes, more preferably between about 10 and about 500,000 centistokes, most preferably between about 10 and about 300,000 centistokes, at 25° C. Silicone oils suitable for use herein include, but are not limited to, polyalkyl siloxanes, polyaryl siloxanes, polyalkylaryl siloxanes, polyether siloxane copolymers, and mixtures thereof. Other insoluble, non-volatile silicone fluids having hair conditioning properties can also be used. A preferred volatile silicone is decamethylcyclopentasiloxane (cylcomethicone D5), supplied by General Electric Corporation.

C. Other Optional Ingredients

The aerosol hair spray compositions of the present invention may, in some embodiments, further comprise optional components known or otherwise effective for use in hair care or personal care products, provided that the optional components are physically and chemically compatible with the essential components described herein, or do not otherwise unduly impair product stability, aesthetics or performance. The concentration of such optional ingredients generally ranges from zero to about 25%, more typically from about 0.05% to about 25%, even more typically from about 0.1% to about 15%, by weight of the composition.

Non-limiting examples of optional ingredients include preservatives, surfactants, styling polymers other than and in addition to the silicone-grafted copolymers described herein, thickeners and viscosity modifiers, electrolytes, fatty alcohols, anti-dandruff actives, pediculocides, skin actives, pH adjusting agents, fragrances, perfume oils, perfume solubilizing agents, sequestering agents, emollients, lubricants and penetrants such as various lanolin compounds, protein hydrolysates and other protein derivatives, ethylene adducts and polyoxyethylene cholesterol, sunscreens, and volatile and non-volatile silicone fluids other than and in addition to the silicone fluids described herein.

III. Methods of Manufacture

The aerosol hair spray compositions of the present invention may be prepared by any known or otherwise effective technique, suitable for providing an aerosol hair spray composition provided that the first and second silicone-grafted copolymers are formulated to have and provide the requisite dichotomous viscosity characteristics defined herein. Methods for preparing the aerosol hair spray compositions of the present invention include conventional formulation and mixing techniques. Suitable methods include two main parts: the preparation of the aerosol concentrate, and the aerosolization of that concentrate.

To prepare the aerosol concentrate, add solvents (ethanol, isoparraffins) to an appropriately sized container. Begin mixing with an agitator capable of producing vigorous agitation. Add copolymers to the solvents slowly to avoid clumping. Mix until copolymers are completely solubilized. Add neutralizer and mix until homogeneous. Add remaining ingredients (except propellants) allowing each to be fully incorporated before adding the next ingredient. After all ingredients have been added, allow to mix for 10–15 minutes to assure homogeneity.

To aerosolize the concentrate, fill it into a suitable container, such as an aerosol dispenser, and then add propellant to that container. This may be done by any of the methods commonly accepted in the aerosol industry. Finally, fit the container with an actuator, such as a spray button.

The aerosol hair spray compositions of the present invention can be contained or dispensed in any known or otherwise effective aerosol container or delivery system. All such containers or delivery systems should be compatible with the essential and any selected optional ingredients of the hair spray composition of the present invention.

Alternatively, pressurized aerosol dispensers can be used where the propellant is separated from contact with the hair spray composition by use of specialized containers such as a two compartment can of the type sold under the trade name SEPRO from American National Can Corporation.

Other suitable aerosol dispensers include those containing compressed air propellant which can be filled into the dispenser by means of a pump or equivalent device prior to use. Such dispensers are described in U.S. Pat. No. 4,077,441 (Olofsson), issued Mar. 7, 1978; and U.S. Pat. No. 4,850,577 (TerStege), issued Jul. 25, 1989. Compressed air aerosol containers suitable for use are also currently marketed by The Procter & Gamble Company under their trade name VIDAL SASSOON AIRSPRAY® hair sprays.

IV. Methods Of Use

The aerosol hair spray compositions of the present invention are used in a conventional manner for providing hairstyle/hold benefits. An effective amount of the composition is sprayed onto dry or damp hair before and/or after the hair is styled. As used herein "effective amount" means an amount sufficient to provide the hair volume and style performance desired, according to the length and texture of the hair.

ANALYTICAL METHODS

Several of the parameters used to characterize elements of the present invention, including molecular weight and molecular weight distribution, are to be quantified by particular experimental analytical procedures. Those procedures are described below.

The molecular weights and molecular weight distributions of copolymers suitable for use in the aerosol hair spray compositions of the present invention may be determined by Size Exclusion Chromatography (SEC) techniques well known in the art. One such technique includes separation of the molecules by the use of a cross-linked polystyrene-divinylbenzene column (MW range=100–107), a differential refractive index detector, and a differential viscometer. A universal calibration curve is prepared from monodispersed polystyrene standards of known molecular weight (MW) and molecular weight distribution (MWD). MW and MWD of the given polymer are determined based on concentration and viscosity responses relative to the calibration. This method for measuring the molecular weights of the silicone-grafted copolymers of the present invention, using gel permeation chromatography (GPC) with refractive index and differential viscometric detection, is detailed below.

A. Principle

Polymer samples are dissolved in tetrahydrofuran (THF) containing toluene. The sample is chromatographed using a series of GPC columns with a THF mobile phase. Detection is by refractive index and differential viscometric detection. Changes in flow rate are adjusted using the toluene as a time retention marker. A universal calibration curve using polystyrene standards is constructed and used to determine sample molecular weight.

GPC separation involves separation through hydrodynamic volume of the molecular distribution. Universal calibration is based on the theories of Flory who showed theoretically that the hydrodynamic volume of a molecule in solution is proportional to the molecular weight times the intrinsic viscosity. Benoit showed that polymers of different chemical structures will fall on the same calibration plot if the parameter of intrinsic viscosity is accounted for in the calibration. The GPC-Viscometry module of the Viscotek software uses the continuous intrinsic viscosity distribution and a molecular weight times intrinsic viscosity calibration curve to account for changes in chemical structure to generate true molecular weights and molecular weight distributions of polymer samples.

B. Equipment

| HPLC | Variain 5000 or 9010, or HP1050 or HP1100 series pump and autosampler or equivalent |
|---|---|
| RI Detector | Waters 410 Refractive Index or equivalent |
| DV Detector | Viscotek Model 100 or H502B differential viscometer or equivalent |
| Data System | Viscotek Trisec Version 2.7 or equivalent |
| Balance | Accurate to 0.0001 g |
| Volumetric Flasks with stoppers | 1000 ml |
| Volumetric Pipets | 20 ml, 10 ml |
| Autosampler Vials & Caps | for use with appropriate autosampler |
| Glass vials | 8 dram and 4 dram Scintillation vials with Teflon lined screw caps |

C. Reagents

1. Tetrahydrofuran, 99.5+%, J. T. Baker HPLC grade, stabilized with 250 ppm BHT, Cat. #JT9440-3

2. Toluene, 99+%, J. T. Baker, Cat. #JT9460-3

3. Polystyrene molecular weight standards, set of 12, individual TSK standards, TOSOH Corporation D. System Suitability As a system check, a polymer check sample should be analyzed to insure the system is operating properly. NBS706 is a National Bureau of Standards polystyrene sample of known molecular weight. When preparing to analyze samples, NBS 706 should be analyzed as a check sample. The Mw for NBS706 should be 257k+/−30k. If the Mw for NBS706 falls outside of this range, this would indicate that the GPC system may not be operating properly, and should be checked by a trained analyst.

E. Experimental Procedure

1. Preparation of Sample/Standard Diluting Solvent

Transfer 100 $\mu$l toluene into a 1000 ml volumetric flask. Add tetrahydrofuran to volume and mix well. The resulting solution contains 100 ppm toluene (as a retention time market) in tetrahydrofuran.

2. Preparation of Polystyrene Calibration Standard Solutions a) Using the following table, transfer the amount listed of each TOSO polystyrene Mw standard into a separate 8 dram vial (vial equipped with Teflon-lined screw cap).

| TOSO Standard | Amount |
|---|---|
| A-2500 | 0.0200 g |
| A-5000 | 0.0200 g |
| F-2 | 0.0200 g |
| F-4 | 0.0200 g |
| F-10 | 0.0100 g |
| F-20 | 0.0100 g |
| F-40 | 0.0100 g |
| F-80 | 0.0100 g |
| F-128 | 0.0050 g |
| F-288 | 0.0050 g |
| F-450 | 0.0050 g |
| F-700 | 0.0050 g | b) Add by pipet exactly 20.0 ml sample/standard diluting solvent to each vial. Cap each vial securely, but do not agitate. Allow to sit overnight, then mix gently by hand. These solutions can be kept indefinitely, provided that they are stored in a refrigerator (4–6° C.) and securely sealed (screw cap and parafilm).

c) Transfer a small portion of each standard solution into separate auto-sampler vials for GPC analysis.

3. Preparation of Polymer Samples a) Weigh 0.040 g (±0.001 g) polymer directly into a tared 4 dram scintillation vial equipped with a Teflon-lined screw cap.

b) Add by pipet exactly 10.0 ml sample/standard diluting solvent. Cap the vial securely, but do not agitate. Allow to sit overnight, then mix gently by hand.

c) Transfer a small portion to each of three auto-sampler vials for GPC analysis in triplicate.

4. Chromatography

Samples should be analyzed using the chromatogrpahic conditions described below.

| GPC Columns: | Shodex KF-807 |
|---|---|
| | Shodex KF-806M (Linear) |
| | Waters Ultrastyragel 100 Å |
| Pre-Column: | Shodex KF-800P |
| Column Temperature: | 31.0° C. |
| Mobile Phase: | Tetrahydrofuran, 1.0 ml/min |
| Sample Loop: | 100 $\mu$l |
| RI Detector | Waters 410 |
| | Sensitivity 128 |
| | Scale Factor 100 |
| | Time Constant 1 |
| | Temperature 31.0° C. |
| Differential Viscometer: | Differential Viscometer: Viscotek Model 100 or H502B |
| | Recorder PA Full-Scale 20 |
| | Temperature 31.0*C. |
| | Inlet Pressure (Typical) 18.5 KPA |
| | Diff. Pressure (Typical) 0 PA |
| Flow Split: | 50:50 DV:RI |
| Software: | Viscotek Trisec 2.7 |
| | (Use TOSO F-40 to set peak parameter file) |

F. Molecular Weight Determination

The procedure described below uses the Viscotek software to determine the molecular weight of the polymer sample. This determination can not be done without the software and requires an analyst trained in the use of the software.

1. Peak Parameter File

Polystyrene standard TOSO F-40 should be used to set the peak parameter file. The peak parameter file is used by the software to compensate for detector offset and peak broadening effects.

2. Time Retention Marker

The toluene added to the THF used to prepare the samples is used as a time retention marker to correct for minor flowrate variation. The time retention marker is set to a flow rate of 1.000 using the retention time of the toluene in polystyrene standard TOSO F-40. The flow rate is adjusted as appropriate for all other standards and samples based on this.

3. Universal Calibration Curve

The universal calibration curve is constructed using the narrow polystyrene standards described above. A new calibration file is opened. The file for a polystyrene standard is opened, flow rate is corrected, and smoothing is performed on the differential viscometric trace (one time smoothing with a factor of 9). Appropriate baselines and integration limits (as close to the beginning and end of the peak as possible) are drawn on the RI and DV traces. Under the calculate header, narrow standard is chosen and the results from this standard are added to the calibration curve. This should be done for each calibration standard until the calibration curve is complete. A calibration curve can be used for an extended period of time if there are no obvious changes in the system (i.e., significant change in flow rates, new columns, analysis of polymers which change the chromatography, etc.). The fit order chosen for the calibration curve should be third order.

4. Determination of Molecular Weight and Polydispersity

With the appropriate calibration and peak parameter file open, molecular weight of the sample can be determined. The file for the sample is opened, flow rate is corrected, and smoothing is performed on the differential viscometric trace (one time smoothing with factor of 9). Appropriate baselines and integration limits (as close to the beginning and end of the peak as possible) are drawn on the RI and DV traces. Under the calculate header, molecular weight is chosen. Results can be shown and printed from the Results header as a MWD summary report. Under the advanced options header, a third order plot fit should be chosen and averages should be computed from unfitted data.

EXAMPLES

The following are non-limiting examples of the aerosol hair sprays compositions of the present invention. The examples further describe and demonstrate embodiments within the scope of the present invention. The examples are given solely for the purpose of illustration and are not to be construed as limitations of the present invention, as many variations thereof are possible without departing from the spirit and scope of the invention, which would be recognized by one of ordinary skill in the art. In the examples, all concentrations are listed as weight percent, unless otherwise specified.

A. Examples of First Silicone-Grafted Copolymer (Monomer ratios are expressed on a weight percentage as charge to the reactor. Polysiloxane-containing monomer S1 has a molecular weight of about 10,000.)

| Copolymer # 1 | 60/20/20 | t-butyl acrylate/acrylic acid/polysiloxane-containing monomer S1 (135,000 wt. avg. mw copolymer) |
|---|---|---|
| Copolymer # 2 | 70/10/20 | t-butyl acrylate/acrylic acid/polysiloxane-containing monomer S1 (160,000 wt. avg. mw copolymer) |
| Copolymer # 3 | 65/15/20 | t-butyl methacrylate/acrylic acid/polysiloxane-containing monomer S1 (110,000 wt. avg. mw copolymer) |
| Copolymer # 4 | 75/15/10 | t-butyl acrylate/acrylic acid/polysiloxane-containing monomer S1 (90,000 wt. avg. mw copolymer) |

B. Examples of Second Silicone-grafted Copolymer (Monomer ratios are expressed on a weight percentage as charge to the reactor. Polysiloxane-containing monomer S1 has a molecular weight of about 10,000. Polysiloxane-containing monomer S2 has a molecular weight of about 20,000.)

| Copolymer # 5 | 80/20 | t-butyl acrylate/polysiloxane-containing monomer S1 (1,000,000 wt. avg. mw copolymer) |
|---|---|---|
| Copolymer # 6 | 75/25 | t-butyl acrylate/polysiloxane-containing monomer S1 (700,000 wt. avg. mw copolymer) |
| Copolymer # 7 | 80/20 | t-butyl acrylate/polysiloxane-containing monomer S2 (1,300,000 wt. avg. mw copolymer) |
| Copolymer # 8 | 85/15 | t-butyl acrylate/polysiloxane-containing monomer S1 (900,000 wt. avg. mw copolymer) |

C. Examples of Aerosol Hair Spray Compositions of the Present Invention

Each of the exemplified compositions below are in the form of an aerosol hair spray, comprising a concentrate and a propellant, which is suitable for application using an aerosol dispenser. As used herein, the abbreviated term "KOH" designates potassium hydroxide solution, containing 45% potassium hydroxide and 55% water and minors, and the abbreviated term "AMP" designates 2-amino-2-methyl-1-propanol. The asterisk (*) designates a volatile branched hydrocarbon supplied by Exxon Corporation. Many perfumes are available to be used in the following examples. A preferred perfume is Elyssa 100A, supplied by The Proctor & Gamble Company. The ratio expressed below each example is the ratio, by weight, of first silicone-grafted copolymer to second silicone-grafted copolymer.

Example I

| Component | Weight, % |
|---|---|
| Ethanol | Q.S. to 100% |
| Isopar C (*) | 22.7% |
| Copolymer #1 | 5% |
| Copolymer #5 | 1% |
| Potassium Hydroxide (45% active) | 1.4 |
| Diisobutyl adipate | 0.5% |
| Perfume | 0.4% |
| Panthenol | 0.04 |
| Dimethyl ether | 35% |
| 80% KOH Neutralized | |
| Ratio 5:1 | |

Example II

| Component | Weight, % |
|---|---|
| Ethanol | Q.S. to 100% |
| Isopar C (*) | 15% |

-continued

| Component | Weight, % |
|---|---|
| Isopar G (*) | 5% |
| Copolymer #2 | 3% |
| Copolymer #6 | 0.5% |
| Potassium Hydroxide (45% active) | 0.42% |
| Diisobutyl adipate | 0.6% |
| Perfume | 0.4% |
| Panthenol | 0.04 |
| Dimethyl ether | 35% |
| 80% KOH Neutralized | |
| Ratio 6:1 | |

Example III

| Component | Weight, % |
|---|---|
| Ethanol | Q.S. to 100% |
| Isopar C (*) | 12% |
| Isopar G (*) | 3% |
| Copolymer #1 | 5.5% |
| Copolymer #5 | 0.5% |
| Potassium Hydroxide (45% active) | 0.86% |
| Aminomethyl propanol | 0.60% |
| Diisobutyl adipate | 0.10% |
| Perfume | 0.4% |
| Panthenol | 0.04 |
| Dimethyl ether | 40% |
| 90% Neutralized [45% KOH/45% AMP] | |
| Ratio 11:1 | |

Example IV

| Component | Weight, % |
|---|---|
| Ethanol | Q.S. to 100% |
| Isopar C (*) | 10% |
| Isopar G (*) | 10% |
| Copolymer #3 | 4.5% |
| Copolymer #7 | .75% |
| Potassium Hydroxide (45% active) | 0.70% |
| Aminomethyl propanol | 0.25% |
| Dipropylene Glycol | 0.40% |
| Perfume | 0.4% |
| Panthenol | 0.08 |
| Dimethyl ether | 30% |
| A46 Propellant | 10% |
| 90% Neutralized [60% KOH/30% AMP] | |
| Ratio 6:1 | |

Example V

| Component | Weight, % |
|---|---|
| Ethanol | Q.S. to 100% |
| Isopar C (*) | 20% |
| Isopar G (*) | 5% |
| Copolymer #4 | 5.5% |
| Copolymer #8 | 1.0% |
| Potassium Hydroxide (45% active) | 0.43% |
| Aminomethyl propanol | 0.61% |
| Propylene Glycol | 0.80% |
| Perfume | 0.4% |

-continued

| Component | Weight, % |
|---|---|
| Phenyl Trimethicone | 0.60% |
| Dimethyl ether | 30% |
| 90% Neutralized [30% KOH/60% AMP] | |
| Ratio 5.5:1 | |

Example VI

| Component | Weight, % |
|---|---|
| Ethanol | Q.S. to 100% |
| Isopar C (*) | 10% |
| Isopar E (*) | 5% |
| Copolymer #4 | 2% |
| Copolymer #5 | 0.5% |
| Aminomethyl propanol | 0.42% |
| Diisobutyl adipate | 0.60% |
| Perfume | 0.4% |
| Phenyl Trimethicone | 1.00% |
| Dimethyl ether | 25% |
| A46 Propellant | 10% |
| 90% AMP Neutralized | |
| Ratio 5:1 | |

Example VII

| Component | Weight, % |
|---|---|
| Ethanol | Q.S. to 100% |
| Isopar C (*) | 15% |
| Copolymer #1 | 2.0% |
| Copolymer #8 | 0.3% |
| Potassium Hydroxide (45% active) | 0.55% |
| Diisobutyl adipate | 0.40% |
| Propylene Glycol | 0.20% |
| Cyclomethicone D5 | 0.50% |
| Perfume | 0.4% |
| A46 Propellant | 30% |
| 80% KOH Neutralized | |
| Ratio 6.7:1 | |

Example VIII

| Component | Weight, % |
|---|---|
| Ethanol | Q.S. to 100% |
| Isopar C (*) | 35% |
| Copolymer #1 | 2.8% |
| Copolymer #8 | 1.2% |
| Potassium Hydroxide (45% active) | 0.87% |
| Diisobutyl adipate | 0.20% |
| Phenyl Trimethicone | 0.10% |
| Cyclomethicone D5 | 0.30% |
| Perfume | 0.6% |
| Dimethyl Ether | 25% |
| A46 Propellant | 10% |
| 90% KOH Neutralized | |
| Ratio 2.3:1 | |

Example IX

| Component | Weight, % |
| --- | --- |
| Ethanol | Q.S. to 100% |
| Isopar C (*) | 13% |
| Isopar E (*) | 13% |
| Copolymer #2 | 6.0% |
| Copolymer #6 | 0.5% |
| Aminomethyl propanol | 0.67% |
| Diisobutyl adipate | 0.10% |
| Perfume | 0.2% |
| Panthenol | 0.05 |
| Dimethyl ether | 35% |
| A46 | 5% |
| 90% AMP neutralized | |
| Ratio 12:1 | |

Example X

| Component | Weight, % |
| --- | --- |
| Ethanol | Q.S. to 100% |
| Isopar C (*) | 13% |
| Copolymer #4 | 4.5% |
| Copolymer #8 | 1.5% |
| Potassium Hydroxide (45% active) | 0.93% |
| Perfume | 0.4% |
| Panthenol | 0.04 |
| Dimethyl ether | 20% |
| Dymel 152a | 10% |
| 80% KOH neutralized | |
| Ratio 3:1 | |

Example XI

| Component | Weight, % |
| --- | --- |
| Ethanol | Q.S. to 100% |
| Isopar G (*) | 10.3% |
| Copolymer #3 | 3% |
| Copolymer #5 | 0.5% |
| Aminomethyl propanol | 0.53% |
| Dipropylene Glycol | 0.05% |
| Perfume | 0.1% |
| Panthenol | 0.1% |
| A31 | 27% |
| 95% AMP neutralized | |
| Ratio 6:1 | |

Example XII

| Component | Weight, % |
| --- | --- |
| Ethanol | Q.S. to 100% |
| Isopar C (*) | 5% |
| Isopar G (*) | 2% |
| Copolymer #1 | 5.5% |
| Copolymer #5 | 1% |
| Potassium Hydroxide (45% active) | 1.52% |
| Propylene Glycol | 0.10% |
| Perfume | 0.2% |

-continued

| Component | Weight, % |
| --- | --- |
| Panthenol | 0.1% |
| Dimethyl ether | 40% |
| 80% KOH neutralized | |
| Ratio 5.5:1 | |

Example XIII

| Component | Weight, % |
| --- | --- |
| Ethanol | Q.S. to 100% |
| Isopar C (*) | 7% |
| Copolymer #2 | 4.5% |
| Copolymer #5 | 0.5% |
| Potassium Hydroxide (45% active) | 0.70% |
| Dipropylene Glycol | 0.07% |
| Perfume | 0.2% |
| Panthenol | 0.5% |
| A31 | 10% |
| Dimethyl ether | 20% |
| 90% KOH neutralized | |
| Ratio 9:1 | |

Example XIV

| Component | Weight, % |
| --- | --- |
| Ethanol | Q.S. to 100% |
| Isopar C (*) | 13% |
| Isopar E (*) | 2% |
| Copolymer #3 | 5.5% |
| Copolymer #7 | 0.71% |
| Potassium Hydroxide (45% active) | 0.46% |
| Aminomethyl Propanol | 0.77% |
| Perfume | 0.2% |
| Panthenol | 0.1% |
| Dimethyl ether | 40% |
| 50% KOH neutralized/45% AMP neutralized | |
| Ratio 7.7:1 | |

Example XV

| Component | Weight, % |
| --- | --- |
| Ethanol | Q.S. to 100% |
| Isopar C (*) | 28% |
| Copolymer #4 | 1.5% |
| Copolymer #7 | 0.5% |
| Potassium Hydroxide (45% active) | 0.31% |
| Diisobuyl Adipate | 0.2% |
| Perfume | 0.3% |
| Panthenol | 0.1% |
| Dimethyl ether | 35% |
| 80% KOH neutralized | |
| Ratio 3:1 | |

What is claimed is:
1. An aerosol hair spray composition comprising:
   A) from about 0.1% to about 10% by weight of said composition, of a first silicone-grafted copolymer comprising a vinyl polymeric backbone and a polysiloxane macromer grafted to said vinyl polymeric backbone,
      i) wherein said first silicone-grafted copolymer is formed from the copolymerization of randomly repeating hydrophilic monomer units, herein designated A, hydrophobic monomer units, herein designated B, and at least one polysiloxane macromer, a) wherein said vinyl polymeric backbone comprises from about 10% to about 50%, by weight of said first silicone-grafted copolymer, of copolymerizable hydrophilic A monomers,
b) wherein said vinyl polymeric backbone comprises from 0% to about 85%, by weight of said first silicone-grafted copolymer, of copolymerizable hydrophobic B monomers,
c) wherein said first silicone-grafted copolymer comprises from about 5% to about 50%, by weight of said first silicone-grafted copolymer, of polysiloxane macromers,
ii) wherein said polysiloxane macromer has a weight average molecular weight from about 500 to about 50,000; and
iii) wherein said first silicone-grafted copolymer has a weight average molecular weight from about 10,000 to about 500,000,
B) from about 0.1% to about 5% by weight of said composition, of a second silicone-grafted copolymer, comprising a vinyl polymeric backbone and a polysiloxane macromer grafted to said vinyl polymeric backbone,
i) wherein said second silicone-grafted copolymer is formed from the copolymerization of randomly repeating hydrophobic monomer units, herein designated B and at least one polysiloxane macromer,
a) wherein said vinyl polymeric backbone comprises from 60% to about 90%, by weight of said second silicone-grafted copolymer, of copolymerizable hydrophobic B monomers,
b) wherein said second silicone-grafted copolymer comprises from about 10% to about 40%, by weight of said second silicone-grafted copolymer, of polysiloxane macromers,
ii) wherein said polysiloxane macromer has a weight average molecular weight from about 5,000 to about 50,000,
iii) wherein said second silicone-grafted copolymer has a weight average molecular weight from about 300,000 to about 5,000,000, and
iv) wherein said first silicone-grafted copolymer is present, relative to said second silicone-grafted copolymer, by weight, in a ratio from about 2:1 to about 26:1;
C) a neutralizing system,
i) wherein said neutralizing system comprises as least one base selected from the group consisting of an organic base, an inorganic base, and mixtures thereof,
ii) wherein said neutralizing system is added at a level sufficient to neutralize from about 30% to about 95% of the acid groups on said first silicone-grafted copolymer;
D) from about 20% to about 50% by weight of said composition, of a propellant and
E) the balance comprising a carrier,
i) wherein said carrier is suitable for solubilizing said first and said second silicone-grafted copolymers, and
wherein said carrier is suitable for application to hair and wherein said composition contains less than about 3% by weight of water.

2. A composition according to claim 1, further comprising up to about 2%, by weight, of a plasticizer.

3. A composition according to claim 1, further comprising from about 0.01% to about 5% of a conditioning agent.

4. A composition according to claim 1, wherein said first silicone-grafted copolymer is selected from the group consisting of:
(i) t-butyl acrylate/acrylic acid/polydimethylsiloxane macromer—10,000 wt. avg. mw macromer (60/20/20);
(ii) t-butyl acrylate/acrylic acid/polydimethylsiloxane macromer—10,000 wt. avg. mw macromer (70/10/20);
(iii) t-butyl methacrylate/acrylic acid/polydimethylsiloxane macromer—10,000 wt. avg. mw macromer (65/15/20);
(iv) t-butyl acrylate/acrylic acid/polydimethylsiloxane macromer—10,000 wt. avg. mw macromer (75/15/10);
(v) and mixtures thereof.

5. A composition according to claim 1, wherein said second silicone grafted copolymer is selected from the group consisting of:
(i) t-butyl acrylate/polydimethylsiloxane macromer—10,000 wt. avg. mw macromer (80/20);
(ii) t-butyl acrylate/polydimethylsiloxane macromer—10,000 wt. avg. mw macromer (75/25);
(iii) t-butyl acrylate/polydimethylsiloxane macromer—20,000 wt. avg. mw macromer (80/20);
(iv) t-butyl acrylate/polydimethylsiloxane macromer—10,000 wt. avg. mw macromer (85/15);
and mixtures thereof.

6. A composition according to claim 1, wherein said vinyl polymeric backbone of said first silicone-grafted copolymer comprises hydrophilic A monomers selected from the group consisting of acrylic acid, methacrylic acid, and mixtures thereof.

7. A composition according to claim 1, wherein said vinyl polymeric backbone of said first silicone-grafted copolymer comprises hydrophobic B monomers selected from the group consisting of n-butyl methacrylate, isobutyl methacrylate, 2-ethylhexyl methacrylate, methyl methacrylate, t-butylacrylate, t-butylmethacrylate, and mixtures thereof.

8. A composition according to claim 1, wherein said vinyl polymeric backbone of said second silicone-grafted copolymer comprises hydrophobic B monomers selected from the group consisting of n-butyl methacrylate, isobutyl methacrylate, 2-ethylhexyl methacrylate, methyl methacrylate, t-butylacrylate, t-butylmethacrylate, and mixtures thereof.

9. A composition according to claim 1, wherein said first silicone-grafted copolymer is present, relative to said second silicone-grafted copolymer, by weight, in a ratio of between 6:1 and 12:1.

10. A composition according to claim 1, wherein said neutralizing system comprises bases selected from the group consisting of potassium hydroxide, sodium hydroxide, 2-amino-2-methyl-1-propanol, and mixtures thereof.

11. A composition according to claim 1, wherein said propellant is selected from the group consisting of isobutane, n-butane, propane, dimethyl ether, and mixtures thereof.

12. A composition according to claim 1, wherein said carrier is selected from the group consisting of $C_1$–$C_6$ alkanols, $C_7$–$C_{10}$ isoparraffins, and mixtures thereof.

13. A composition according to claim 2, wherein said plasticizer is selected from the group consisting of diisobutyladipate, propylene glycol, dipropylene glycol and mixtures thereof.

14. A composition according to claim 3, wherein said conditioning agent is selected from the group consisting of phenyl trimethicone, decamethylcyclopentasiloxane, panthenol, and mixtures thereof.

15. A method of styling hair comprising applying to the hair an effective amount of a composition according to claim 1.

16. Process of making an aerosol hair spray composition, containing less than about 3% by weight of water, for which the process of making comprises the following steps:
1) mixing the following ingredients to form a homogenous mixture:
   A) from about 0.1% to about 10% by weight of said composition, of a first silicone-grafted copolymer comprising a vinyl polymeric backbone and a polysiloxane macromer grafted to said vinyl polymeric backbone,
      i) wherein said first silicone-grafted copolymer is formed from the copolymerization of randomly repeating hydrophilic monomer units, herein designated A, hydrophobic monomer units, herein designated B, and at least one polysiloxane macromer,
         a) wherein said vinyl polymeric backbone comprises from about 10% to about 50%, by weight of said first silicone-grafted copolymer, of copolymerizable hydrophilic A monomers,
         b) wherein said vinyl polymeric backbone comprises from 0% to about 85%, by weight of said first silicone-grafted copolymer, of copolymerizable hydrophobic B monomers,
         c) wherein said first silicone-grafted copolymer comprises from about 5% to about 50%, by weight of said first silicone-grafted copolymer, of polysiloxane macromers,
      ii) wherein said polysiloxane macromer has a weight average molecular weight from about 500 to about 50,000; and
      iii) wherein said first silicone-grafted copolymer has a weight average molecular weight from about 10,000 to about 500,000,
   B) from about 0.1% to about 5% by weight of said composition, of a second silicone-grafted copolymer, comprising a vinyl polymeric backbone and a polysiloxane macromer grafted to said vinyl polymeric backbone,
      i) wherein said second silicone-grafted copolymer is formed from the copolymerization of randomly repeating hydrophobic monomer units, herein designated B and at least one polysiloxane macromer,
         a) wherein said vinyl polymeric backbone comprises from 60% to about 90%, by weight of said second silicone-grafted copolymer, of copolymerizable hydrophobic B monomers,
         b) wherein said second silicone-grafted copolymer comprises from about 10% to about 40%, by weight of said second silicone-grafted copolymer, of polysiloxane macromers,
      ii) wherein said polysiloxane macromer has a weight average molecular weight from about 5,000 to about 50,000,
      iii) wherein said second silicone-grafted copolymer has a weight average molecular weight from about 300,000 to about 5,000,000, and
      iv) wherein said first silicone-grafted copolymer is present, relative to said second silicone-grafted copolymer, by weight, in a ratio from about 2:1 to about 26:1;
   C) a carrier.
      i) wherein said carrier is suitable for solubilizing said first and said second silicone-grafted copolymers, and
      ii) wherein said crier is suitable for application to hair, and
   D) a neutralizing system;
      i) wherein said neutralizing system comprises at least one base selected from the group consisting of an organic base, an inorganic base, and mixtures thereof, and
      ii) wherein said neutralizing system is added at a level sufficient to neutralize from about 30% to about 95% of acid groups on said first silicone-grafted copolymer and
2) aerosolizing the homogenous mixture of step 1, using from about 20% to about 50% by weight of said composition, of a propellant.

17. The process of making the aerosol hair spray composition of claim 16, wherein the ingredients of step 1 are added and mixed in the following order: the carrier, the first silicone-grafted copolymer, the second silicone-grafted copolymer, and then the neutralizing system.

18. The process of making the aerosol hair spray composition of claim 16, wherein the ingredients of step 1 are added and mixed in the following order: the carrier, the second silicone-grafted copolymer, the first silicone-grafted copolymer, and then the neutralizing system.

19. A method of styling hair comprising applying to the hair an effective amount of the aerosol hair spray composition made according to the process of claim 16.

* * * * *